United States Patent [19]

Hochstein

[11] Patent Number: 4,798,956
[45] Date of Patent: Jan. 17, 1989

[54] ELECTRO-OPTICAL WINDSHIELD MOISTURE SENSING

[76] Inventor: Peter A. Hochstein, 2966 River Valley Dr., Troy, Mich. 48098

[21] Appl. No.: 73,496

[22] Filed: Jul. 15, 1987

[51] Int. Cl.$^4$ .............................................. G01N 21/41
[52] U.S. Cl. ................................... 250/341; 15/250 C; 250/339; 250/349
[58] Field of Search ................ 250/341, 349, 339; 15/250 C; 318/444, 483, 480, DIG. 2

[56] References Cited

U.S. PATENT DOCUMENTS

| | | | |
|---|---|---|---|
| 3,291,590 | 12/1966 | McMaster | 65/182 |
| 3,307,095 | 2/1967 | Redmond | 318/483 |
| 3,555,289 | 1/1971 | Sobkow | 307/10 R |
| 3,594,563 | 7/1971 | Bishop . | |
| 3,619,614 | 11/1971 | Yamaka . | |
| 3,660,659 | 5/1972 | Eisenman et al. . | |
| 3,689,814 | 9/1972 | Holt | 318/266 |
| 3,743,056 | 7/1973 | Zitelli et al. | 187/29 R |
| 3,786,330 | 1/1974 | Inoue et al. | 318/483 |
| 3,826,979 | 7/1974 | Steinmann | 324/61 R |
| 3,925,244 | 12/1975 | Nagasawa et al. | 250/372 |
| 3,977,792 | 8/1976 | Jumonji et al. | 356/445 |
| 4,010,383 | 3/1977 | Grassmann | 304/118 |
| 4,131,834 | 12/1978 | Blaszkowski | 318/483 |
| 4,139,801 | 2/1979 | Linares | 315/83 |
| 4,229,653 | 10/1980 | Uthe | 250/339 |
| 4,317,073 | 2/1982 | Blaszkowski | 318/483 |
| 4,339,698 | 7/1982 | Kearns | 318/444 |
| 4,355,271 | 10/1982 | Noack | 318/480 |
| 4,394,605 | 7/1983 | Terazawa | 318/280 |
| 4,463,294 | 7/1984 | Gibson | 318/313 |
| 4,476,419 | 10/1984 | Fukatsu et al. | 318/444 |
| 4,481,450 | 11/1984 | Watanabe et al. | 318/444 |
| 4,495,452 | 1/1985 | Boegh-Peterson | 318/444 |
| 4,588,935 | 5/1986 | Kaneiwa et al. | 318/483 |
| 4,589,771 | 5/1986 | Watanabe et al. | 356/38 |
| 4,595,866 | 6/1986 | Fukatsu et al. | 318/444 |
| 4,620,141 | 10/1986 | McCumber et al. | 318/483 |
| 4,636,643 | 1/1987 | Nakamura et al. | 250/338 |
| 4,652,745 | 3/1987 | Zanardelli | 250/227 |
| 4,676,638 | 6/1987 | Yasuda | 356/237 |

FOREIGN PATENT DOCUMENTS

| | | | |
|---|---|---|---|
| 3206029 | 4/1983 | Fed. Rep. of Germany . | |
| 3244767 | 6/1984 | Fed. Rep. of Germany | 15/250 C |
| 22945 | 2/1982 | Japan | 15/250 C |
| 185339 | 10/1983 | Japan . | |
| 199253 | 11/1983 | Japan | 15/236.01 |
| 14563 | 1/1984 | Japan | 15/250 C |
| 89250 | 5/1984 | Japan | 15/250 C |
| 85944 | 5/1984 | Japan | 340/602 |
| 84141 | 5/1984 | Japan . | |
| 106348 | 6/1984 | Japan | 15/250 C |
| 100034 | 6/1984 | Japan . | |
| 78844 | 5/1985 | Japan . | |
| 174931 | 9/1985 | Japan . | |
| 174348 | 9/1985 | Japan . | |
| 216246 | 10/1985 | Japan . | |
| 216245 | 10/1985 | Japan . | |

Primary Examiner—Janice A. Howell
Assistant Examiner—Constantine Hannaher
Attorney, Agent, or Firm—Harold W. Milton, Jr.

[57] ABSTRACT

The invention is a moisture sensor which includes an emitter (18) to emit pulses of radiant energy toward the inside surface (14) of a window (12) at an incident angle ($\theta$). The radiant energy is refracted into the window (12) at the air-inside window surface (14) and reflected off the air-outside window surface (16) back through the window (12). The radiant energy is then detected by a detector (20) at a reflection angle ($\theta'$) equal to the incident angle ($\theta$). A support (22) spaces the emitter (18) and detector (20) a distance D between the intersection (I) of the axis (A) of the emitter (18) with the inside window surface (14) and the intersection (E) of the axis (B) of the detector (20) with the inside window surface (14) which is determined by the formula:

$$D = 2T \cos\theta (n^2 - \cos^2\theta)^{-\frac{1}{2}}$$

The detector (20) includes a collimator (36) to prevent non-parallel radiant energy from entering the detector (20) and an optical filter (40) to filter out radiant energy wavelengths below a predetermined wavelength in order to detect the emitted radiant energy.

28 Claims, 4 Drawing Sheets

ELECTRO-OPTICAL WINDSHIELD MOISTURE SENSING

TECHNICAL FIELD

This invention relates to electro-optical sensors for sensing radiant energy, and more specifically, sensors for sensing moisture on a window by reflecting radiant energy.

BACKGROUND OF THE INVENTION

Automatic rain sensors for controlling the windshield wipers on vehicles have employed many moisture sensing methods including capacitance, resistance, microwave and optical means. Capacitive and resistive sensors are economical and relatively simple but require the application of special coatings to the windshield glass. Functional coatings must be abrasion resistant, aesthetically acceptable, and reliable over the long term. Methods for applying these sensor coatings generally involve techniques that interfere with the normal production process for windshield glass, such as a thin or thick film of conductive material fired into the glass surface.

Optical sensors employ infrared emitters and detectors to determine whether moisture is present on the windshield surface. The advantage of these optical sensors is that they can theoretically be adapted to any windshield without the need for special glass processing. The problem with optical sensors is functioning in direct sunlight or even clear sky conditions.

One type of optical sensor emits radiation into the window wherein it is internally reflected several times and then detected. The radiation is converted to an electrical signal for activating the windshield wipers. Such a system is described in U.S. Pat. No. 4,481,450 issued Nov. 6, 1984 in the name of Takashi Watanabe and assigned to Nippondenso Co., Ltd. This patent discloses an optical sensor on the inside of a window which emits infrared radiation directly into a material comparable with that of the window. The infrared radiation passes into the glass and is reflected several times before being sensed on the inside of the window. An electrical signal is then produced which is representative of the amount of radiation reflected and therefore the amount of moisture on the windshield. A problem with this type of sensor is that the magnitude of the radiated beam is decreased substantially after each reflection making the detection thereof difficult; manufacture of and application of the sensor to the windshield is difficult in order to ensure no air gaps between the sensor, material and glass, and if there are air gaps, refraction of the energy has not been considered. Ambient and direct light may easily saturate the detector and interfere with the operation this sensor making it inoperable.

Another type of optical sensor is described in U.S. Pat. No. 4,355,271 issued Oct. 19, 1982 in the name of Raymond J. Noack. This patent discloses two optical sensors operating from a common emitter. The sensors are spaced to take into account only reflection of the outside surface of the window. One sensor is to sense moisture, the other sensor is to sense dirt or other particles. A problem with this type of sensor assembly is that the refraction at the air-glass surface has not been accounted for. Additionally, incident sunlight falling on the photodetector would easily saturate the sensor rendering the assembly useless.

SUMMARY OF THE INVENTION AND ADVANTAGES

This invention is a sensing assembly and method for indicating when moisture or other particles have accumulated on a window having inside and outside surfaces defining a thickness (T) and of a material having an index of refraction (n). An emitter means is included for disposition on the inside of the window for emitting radiant energy to the window on an ingress axis (A) at an incident angle ($\theta$) relative to the inside surface. A detector means is included for disposition on the inside of the window for detecting radiant energy from the window on an egress axis (B) at a reflection angle ($\theta'$) relative to the inside surface and equal to the incident angle ($\theta$). A support means supports the emitter means and the detector means for spacing the point (I) of intersection of the ingress axis (A) with the inner surface of the window from the point (E) of intersection of the egress axis (B) with the inner surface of the window a predetermined distance (D), the predetermined distance (D) is determined by the formula:

$$D = 2T \cos\theta (n^2 - \cos^2\theta)^{-\frac{1}{2}}$$

The invention also includes limiting means for limiting the field of view of radiant energy from the window entering the detector means by allowing to pass only radiant energy substantially parallel with the egress axis (B) within the field of view.

The advantage of this type of assembly is that there is only one reflection thereby making the assembly less susceptible to ambient light by producing a higher energy signal. Manufacture and application of the assembly is simple by using an autonomous assembly which takes into account the refraction of the air-glass surface. Additionally, by limiting the field of view of the detector, response to ambient light is minimized.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
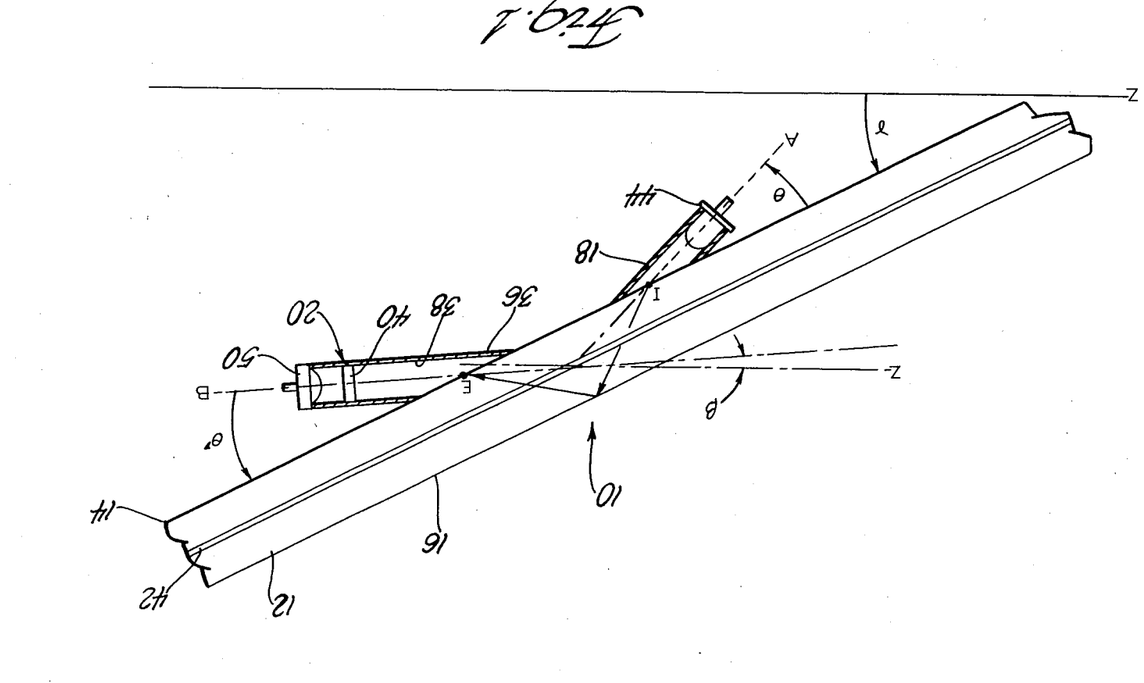
FIG. 1 is a schematic view of the window and sensors of the subject invention.
Figure 2:
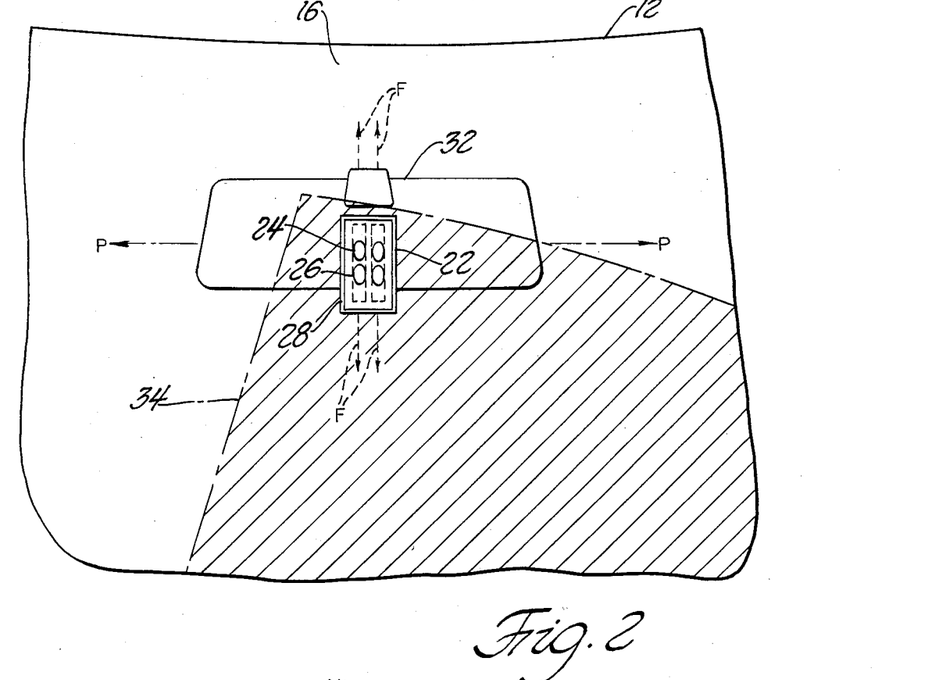
FIG. 2 is a frontal view through the window of the subject invention.

A sensing assembly 10 for indicating when moisture or other particles have accumulated on a window 12 having inside 14 and outside 16 surfaces is generally shown at 10 in FIG. 1. The assembly 10 includes emitter means 18 for disposition on the inside 14 of the window 12 to emit radiant energy toward the window 12, and detector means 20 for disposition on the inside 14 of the window 12 to detect radiant energy from the window 12. A support means 22 spaces the emitter means 18 and the detector means 20. In general, radiant energy is caused to either fully or partly reflect from a glass-air interface. Water droplets on the glass surface cause more energy to be coupled out of the glass into the water droplets. The change in reflectance of the glass-air surface is sensed by the detector means 20 which then provides an output proportional to the amount of water on the glass surface. The window 12 may be made of glass, as is typical, but need not be limited to glass.

Infrared energy is preferably used in automotive application to compensate for surrounding ambient light interference. Commercially available infrared emitters emit energy peaking at approximately 940 nm while solar radiant energy peaks at approximately 500 nm. Reference in the following description makes reference to infrared energy, but it is to be understood that other radiant energy could be used depending on the application.

Figure 3:
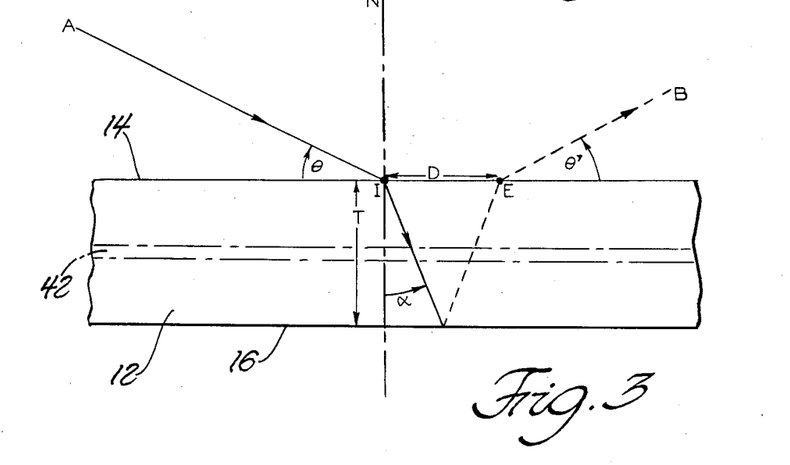
FIG. 3 is a geometrical representation of reflection and refraction angles of the infrared energy beam.

The positioning of the emitter means 18 and the detector means 20 is very critical. As shown in FIGS. 1 and 3, the emitter means 18 produces radiant energy, or more specifically infrared energy, which is directed or emitted toward the window 12 at an incident angle $\theta$ and refracted at an angle $\alpha$ (angle from the normal N) at the air-inside window surface 14. The refracted radiant energy is passed through the window 12 and is then reflected off the air-outside window surface 16 back through the window 12 and out the air-inside window surface 14 at which point it is refracted and angled away from the window 12 at a reflection angle $\theta'$ equal to that of the incident angle $\theta$.

The inside 14 and outside 16 surfaces of the window 12 define a thickness T. The window 12 is of a material having an index of refraction n; the index of refraction also varies with the wavelength of the radiant energy. The emitter means 18 transmits radiant energy toward the window 12 on an ingress axis A at an incident angle $\theta$ relative to the inside surface 14. The detector means 20 receives and detects radiant energy from the window 12 on an egress axis B at a reflection angle $\theta'$ relative to the inside surface 14 equal to the incident angle $\theta$. The emitter means 18 must have the same angular relationship to the window 12 surface as does the detector means 20, because the angle of the incident $\theta$ must equal the angle of reflection $\theta'$. Associated with the window material, is a critical angle for the air-window 12 interface such that when it is approached, most the of incident radiant energy will not penetrate the window 12, but merely reflect off the inside surface 14. The critical angle for most glass-to-air interface is nominally 20°, therefore incident angles $\theta$ less than about 20° will merely be reflected off the inside surface 14 of a glass window 12.

The support means 22 supports the emitter means 18 and the detector means 20 such that the point I of intersection of the ingress axis A with the inside surface 14 of the window 12 from the point E of intersection of the egress axis B with the inside surface 14 of the window 12 is a predetermined distance D. In other words, the emitter means 18 and detector means 20 have an effective beam diameter of radiant energy. Between the central point where these diameters (the ingress axis A and egress axis B) intersect on the inside window surface 14, there is a predetermined distance D therebetween. The predetermined distance D is dependent on the thickness T of the window 12, the incident $\theta$ or reflection $\theta'$ angle, and the index of refraction n determined by the window material 12 and the wavelength of the radiant energy.

The following formula has been developed to determine the distance between the intersection of the ingress axis A of the emitter means 18 with the inside surface 14 of the window 12 and the intersection of the egress axis B of the detector means 20 with the inside surface 14 of the window 12 which is dependent on the index of fraction n, the incident or reflection angle $\theta$, $\theta'$, and the thickness of the glass T:

$$D = 2\,T \cos\theta\,(n^2 - \cos^2\theta)^{-\frac{1}{2}}$$

The support means 22 supports the emitter means 18 and the detector means 20 at the predetermined distance D and angle $\theta, \theta'$ configuration. The support means 22 includes a detector holder means 24 directed toward the window 12 at the reflection angle $\theta'$ associated with a horizon angle $\eta$ directed below the horizon Z. The support means 22 includes emitter holder means 26 for securing the emitter means 18 directed toward the window 12 at the incident angle $\theta$ equal to the reflection angle $\theta'$. The detector holder means 24 and the emitter holder means 26 are angled toward the window 12 at the incident $\theta$ and reflection $\theta'$ angles greater than the critical angle associated with the window material. The emitter holder means 26 and the detector holder means 24 are tubular in shape and circular in cross-section having an outer diameter of the effective beam diameter of radiant energy centered about the ingress A and egress B axes, respectively. The distance between the intersection of the central point of the two holder means 24, 26, or ingress axis A and egress axis B with the inside surface 14 of the window 12, is set by the calculated predetermined distance D. The tubular emitter holder means 26 and the tubular detector holder means 24 partially overlap at their outside diameters at the plane of the window 12. Therefore, the support means 22 includes blocking means 25 at the location of the partial overlapping of the two holder means 24, 26 adjacent the window 12 for blocking radiant energy from the emitter means 18 to the detector means 20 reflected off the inside surface 14 of the window 12. The blocking means 25 may be any type of material which is opaque.

A typical windshield 12 in the modern car is installed at a rake angle $\gamma$ of approximately 30° to horizontal Z for aerodynamic reasons. The subject invention is not limited to this rake angle $\gamma$, but is used merely for example. It is desirable to dispose the angle of the axis B of the detector means 20 below the horizon Z so that direct sunlight can not enter the detector means 20, at least on level pavement. For example, in a window 12 having a rake angle $\gamma$ of 30°, the axis B of the detector means 20 may be angled $\beta = 5°$ below the horizon Z, which will have a reflection angle $\theta'$ of 25°. Obviously, the axis A of the emitter means 18 will have an incident angle $\theta$ also equal to 25° angle. At rake angles $\gamma$ greater than 30°, the detector means 20 may be angled further below the horizon Z. Using the reflection $\theta'$ and incident $\theta$ angles as illustrated above of 25°, the formula for the predetermined distance D can be solved. Assuming the window material is glass and radiant energy is in the infrared range (or more specifically 940 nm), it is known that the index of refraction n for window glass equals 1.51. The thickness T of the window 12 can be measured, using for example 0.210 in (5.334 mm). Substituting these numbers into the formula for the predetermined distance D:

$$D = 2(0.210 \text{ in}) \cos 25° (1.51^2 - \cos^2 25°)^{-\frac{1}{2}}$$

and solving:
D=0.315 inches (8.005 mm)

Therefore, the intersections I and E of the ingress A axis and egress B axis with the inside surface 14 of the window 12 must be 0.315 inches apart, and the support means 22 will hold the emitter means 18 and detector means 20 at this angle $\theta = 25°$ and the distance D=0.315 inches between the axes A, B at the plane of the inside surface 14 of the window 12.

Figure 4:
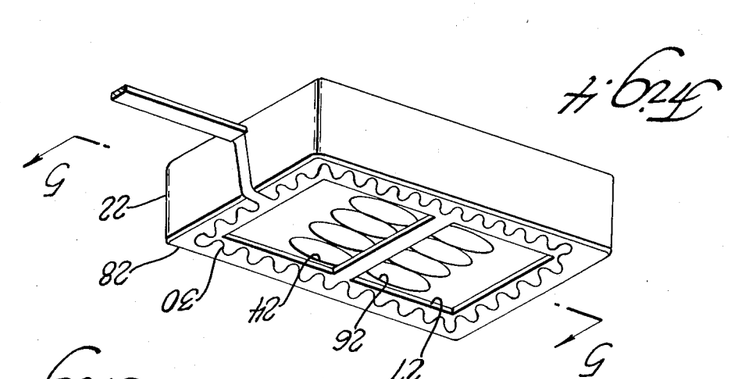
FIG. 4 is a perspective view of the support means of the subject invention.
Figure 5:
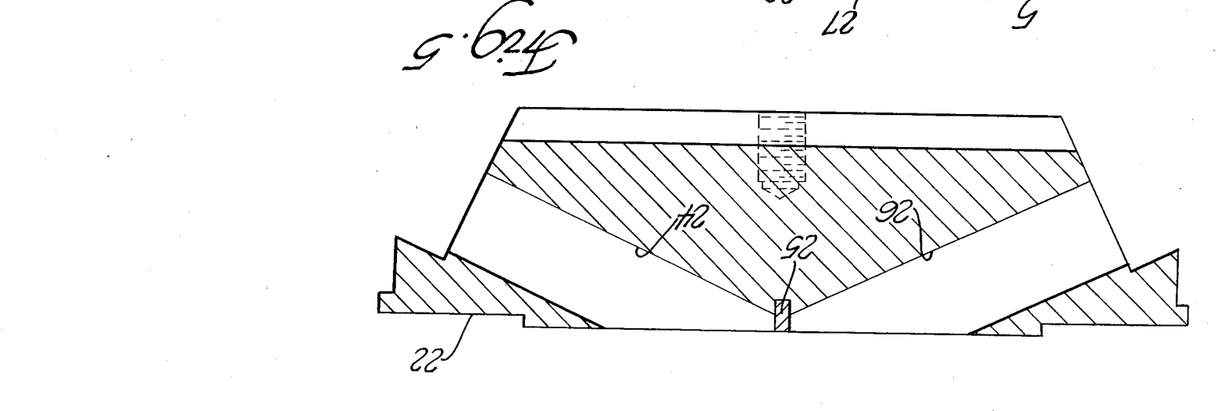
FIG. 5 is a cross-sectional view taken along lines 5—5 of FIG. 4.

In the preferred embodiment, as shown in FIG. 4, it is suggested that a plurality of channels, or pairs of emitter means 18 and detector means 20, be used to aid in the sensitivity of moisture or particles on the window 12, as will be described subsequently. The optical axes of each emitter-detector pair describes a plane F which should be vertical and essentially normal to the plane P of the window 12. In such an attitude, the sensor detectors 20 are least likely to be swamped by the interfering light that may illuminate the window 12.

The support means 22 encapsulates the emitter means 18 and detector means 20. The support means 22 includes openings 27 adjacent the window 12 for allowing the infrared energy to pass from the emitter means 18 and for allowing the light energy to be received by the detector means 20. The support means 22 may include adhering means 28 between the support means 22 and the window 12 excluding the openings 27 for securing the assembly 10 to the window 12 and for preventing contamination of the emitter 18 and detector 20 means. The adhering means 28 may be comprised of foam tape and a seal to prevent moisture and dirt from entering the support means 22.

In automotive use, windshield wiper blades sometimes leave a residual film of water or dirt on the window 12 after each pass. Fine streaks are also prevalent, particularly with older or damaged rubber blades. These artifacts are readily detected by the assembly 10, and needlessly cycle the wipers in an attempt to fully clear the window 12. It has been found that with the vehicle in motion, the streaks of water film clear readily due to the rapid movement of air across the surface. At rest, however, evaporation of these residual films is far slower, and the wipers tend to operate too often. In warm or hot weather, there is a decreased tendency to retain a water film on the glass because evaporation is thermally driven. One method to enhance film evaporation at lower exterior temperatures, is to locally heat the sensed area with heating means 30 on the adhering means 28 in the immediate vicinity of the detector and emitter 18 means. This may be a simple coil of heating wire 30.

Placement of the sensor on the windshield is not critical. However, the support means 22 must be mounted within the wiped area 34 of the wiper blades, preferably in an unobtrusive location. The support means 22 may be attached to the rear view mirror 32 of a vehicle in order not to interfere with sight of the driver.

The detector means 20 includes limiting means 36 for limiting the field of view of radiant energy entering the detector means 20 from the window 12 by allowing to pass only radiant energy substantially parallel with the egress axis B within the field of view. A smaller field of view will be more effective in detecting the reflected-refracted radiant energy decreasing ambient light energy interference, as would happen with a larger field of view. The limiting means 36 may be a collimator wherein the aspect ratio (diameter length ratio) may be chosen to occlude direct sunlight at the horizon Z. The limiting means 36 may include absorbing means 38 coated on the inside of the collimator with a special, black absorbing paint. The paint will prevent light energy from being reflected off the inside of the collimator 36 and sensed by the detector means 20. It should be understood that other types of limiting means 36 may be used, such as a lens. Experiments with optical sensors showed that wiping of the window 12 of a vehicle was desired by an operator when water droplet size was relatively small, such as 0.5–1.0 mm diameter. In order to reliably detect such small water drops, the field of view or sensing area of the emitter-detector means 20 pair had to be kept small, such as under 10 mm diameter, so that the change in reflected infrared energy could be easily discerned. The ratio of areas of a 0.5 mm water drop to 10 mm field of view sensing area would only change the net reflection by less than 0.25 percent. When using a collimator 36, it is suggested using a 5 mm dia×12 mm long tube. During very light rain, automatic wiping action may be desired for small droplets with mean spacings as great as 18 mm. In order to properly sample a representative area of the windshield, two or more sensor pairs could be employed as discussed above. A particularly sensitive rain sensor 10 may be configured with four sensor pairs, as indicated in FIG. 4, in close proximity yielding an effective sensing area of approximately 9 mm×36 mm. Each sensor will work independently, the output of each being logically OR'ed to trigger the wiping mechanism. The above quantities are examples of satisfactory operation variables, but the subject invention is not limited thereto.

The detector means 20 also includes a filter means 40 for receiving the parallel radiant energy to filter out radiation below a predetermined wavelength. The best way to reduce ambient solar interference and enhance the signal to noise ratio of the sensor is to optically filter the detector means 20. In the preferred embodiment, the predetermined wavelength of the filter means 40 approximately equals the radiation wavelength of the emitter means 18. The filter means 40 may be selected to peak at the emitter radiation wavelength. The filter means 40 may be a narrow band filter peaked to the emitter means 18 emissions wavelength which is mounted in the limiting means 36, or collimator tube. The filter means 40 limits the spectral response of the detector means 20 to relatively narrow band centered around the peak emission wavelength of the emitter means 18, typically 940 nm for a Ga As emitter. A filter means 40 with a sharp cutoff in the near infrared for energy of 800 nm and shorter wavelengths can provide a practical, simple narrow band filter for a silicon detector, excluding virtually all visible light.

Most U.S. windshields 12 are laminated and include an interlayer tinting means 42. The interlayer means 42 is used in laminated windshields providing a tinted glass and a PVB (polyvinyl butyral) interlayer 42 for shatter protection. Some windshields use tinted glass with an interlayer 42 for shatter protection, rather than tinting the interlayer. Laminated glass absorbs the radiant energy which quickly attenuates the energy or emitted radiation to useless levels. On a single pass, only nominally 25% on the incident infrared at 940 nm will pass through the tinted inter layer 42. Therefore, high emitter power levels are required in order to detect the infrared energy from the incident sunlight due to the decrease in energy associated with the interlayer means 42. The interlayer means 42 is not required in operation of the assembly 10, but it is compensated for in the assembly 10.

Figure 6:
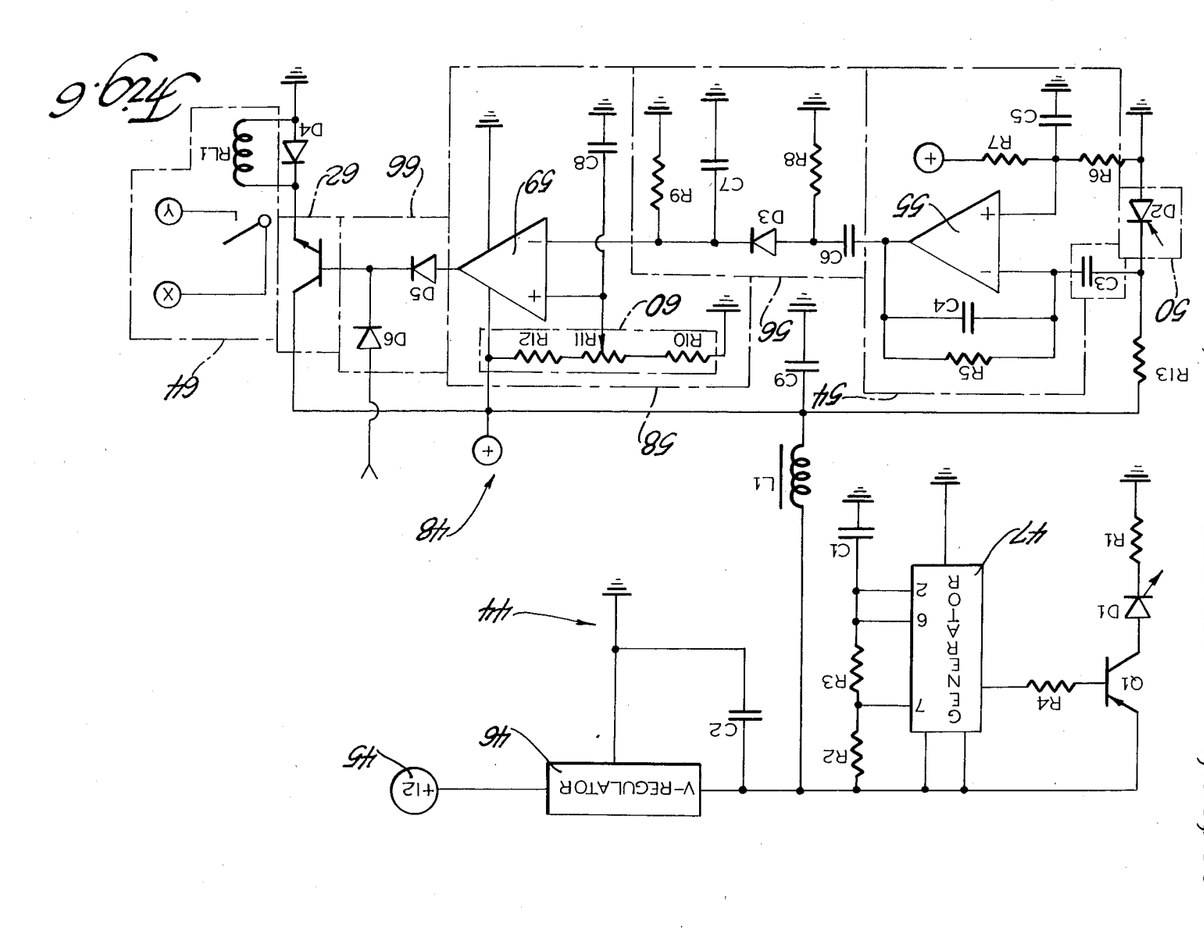
FIG. 6 is a schematic of the emitter and detector control means of the subject invention.

The emitter means 18 includes pulsing means 44 for emitting radiant energy, or more specifically infrared energy, toward the window 12. The pulsing means 44 includes an infrared emitter diode D1. Other radiant energy wavelengths may be pulsed. The pulsing means 44 may be connected to a voltage source, such as the battery 45 of a vehicle. A voltage regulator 46 receives this voltage which is then sent to an astable pulse generator 47. A common emitter transistor Q1 is used as a pulse amplifier for the emitter diode D1. The duty cycle of nominally 10 micro seconds with a repetition rate of 1 KHz minimizes self-heating of the emitter diode D1. A high 1.5 A current for the 10 micro second pulsation of the emitter diode D1 is effectively filtered on the power supply line by a filter capacitor C2. A collector resistor R1 is connected between the emitter diode D1 and ground. The astable pulse generator 47 is externally controlled by a first resistor R2 connected between the power line and pin 7, a second resistor R3 connected between pin 7 and pin 6, and a capacitor C1 connected to pins 6, 2 and ground. An output resistor R4 is connected to the output of the pulse generator 47 and the base of transistor Q1.

The detector means 20 includes a detector control means 48 for detecting the light energy from the window 12 through the limiting means 36 and filter means 40. The detector control means 48 includes an infrared light sensitive means 50 responsive to light energy for producing an electrical signal. The infrared light sensitive means 50 is a filtered photodiode D2 which receives the narrow 1 KHz infrared pulses through the limiting means 36, or collimator. The photodiode D2 is sensitive to visible light as well as infrared energy. The control means 48 includes coupling means 52 for ac coupling the electrical signal to the amplifier means 54. An amplifier means 54 linearly amplifies the magnitude of the electrical signal producing an amplified signal. The photodiode D2 is reversed biased, and ac coupled by the coupling means 52, which is a capacitor C3, to the amplifier means 54 which is an operational amplifier 55 which has a nominal ac gain of 15 with feedback resistor R5 and feedback capacitor C4. The non-inverting pin of the first op-amp includes a voltage divider resistors R6, R7 connected between ground and positive voltage source, and a capacitor C5 connected to ground and the non-inverting pin. The detected electrical signal is proportional to the amount of moisture or water droplets on the outside surface 16 of the window 12. When dry, the outside surface 16 of the window 12 reflects a relatively larger proportion of the illuminating incident infrared energy then when the outside surface 16 has water present. This electrical signal is converted to a proportional dc level by the rectifying network consisting of, capacitor C6, resistor R8, diode D3, capacitor C7, and resistor R9. The control means 48 also includes rectifier means 56 for rectifying the amplified signal to a dc signal to be sent to a comparator means 58. The comparator means 58 receives the dc signal and compares it to a predetermined magnitude to determine the amount of moisture or other particles on the window 12. The comparator means 58 includes an operational amplifier 59 configured as a comparator. The comparator means 58 includes adjustment means 60 for manually varying the predetermined magnitude for setting sensitivity of the assembly 10. The adjustment means 60 is connected to the noninverting pin and comprises a potentiometer R11 between a voltage divider network comprising resistor R10 connected to ground resistor R12 connected to power source connected to the noninverting pin and a capacitor C8 to ground. Whenever the comparator means 58 senses that the proportional dc signal falls below the predetermined magnitude, the output of the comparator means 58 goes high. Dirt or dust collecting on the outside surface of the window, in absence of water, will cause the proportional signal to increase rather than decrease. An additional comparator may be included to sense when the proportional signal is above a magnitude indicating dust on the outside 16 of the window 12. A driving means 62 receives the signal from the comparator means 58 to produce a drive signal. The driving means 62 is an amplifier transistor Q2 configured as an emitter follower current amplifier to pull in a control relay RL1. The relay means 64 actuates a wiper means to remove the detected moisture or particles. A visual indication means in the form of an L.E.D. D4 indicates the presence of the drive signal and the energization of the relay. Contacts on the relay RL1 are be used to actuate the wiper motor directly, or through existing integral cycle controls that are part of most modern wiper systems. Power to the detector may be supplied from the voltage regulator 46 of the emitter means 18 through an isolation choke L1.

Several channels consisting of emitter means 18 and detector means 20 can be operated in parallel. The control means 48 includes combining means 66 for indicating when moisture or other particles have accumulated on the window 12 from a plurality of emitter-detector pairs. The comparator means 58 output of each channel is then OR'ed by the combining means to drive one common control relay as shown. The combining means includes a diode D5, D6 at the output of each of the comparator means 58 of the plurality of emitter-detector pairs to produce the drive signal.

A 1 KHz operating frequency is a good compromise between acceptable emitter means 18 dissipation and immunity to interference from both constant dc and changing light sources. High intensity discharge lamps which emit energy when they flicker at 120 Hz do not affect the sensor even in close proximity to street lamps or building luminaries. The input capacitor C3 in connection with the input impedance of operational amplifier 55 establish the low frequency band pass of the input amplifier 54. While an electro mechanical relay RL1 is shown as the output element, fully solid state switching could also be used.

The general steps in the operation of sensing moisture or other particles on the window 12 includes emitting 18 radiant energy to the window 12 on the ingress axis A at the incident angle $\theta$ relative to the inside surface 14 of the window 12. The radiant energy is pulsed 18 toward the inside surface 14 of the window 12 at high levels to compensate for attenuations of radiant energy levels from the window 12. The radiant energy is then passed through the interlayer 42 within the window 12 attenuating the radiant energy, reflected off the outside surface 16 of the window 12 attenuating the radiant energy, and re-passed through the interlayer attenuating the radiant energy. This radiant energy is then detected 20 from the window 12 on the egress axis B at a reflection angle $\theta'$ relative to the inside surface 14 and equal to the incident angle $\theta$. The point I of intersection of the ingress axis A with the inner surface 14 of the window 12 is spaced from the point E of intersection of the egress axis B with the inner surface 14 of the window 12 a distance D which equals:

$$D = 2\, T \cos\theta\, (n^2 - \cos^2\theta)^{-\frac{1}{2}}$$

Emitted radiant energy reflected off the inside surface 14 of the window 12 is blocked from being detected. The field of view of radiant energy from the inside surface 14 of the window 12 is limited 36 for detecting and only radiant energy substantially parallel with the egress axis B within the field of view is detected. Non-parallel radiant energy is absorbed 38 to prevent the detection thereof. The parallel radiant energy below a predetermined wave length, preferably infrared wavelengths, is filtered 40 therefrom to prevent the detection thereof. Radiant energy at an angle above the horizon and greater than the critical angle of the window 12 is detected.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A sensing assembly (10) using radiant energy for indicating when moisture or other particles have accumulated on a window (12) having inside and outside surfaces (16) thickness (T) and of a material having an index of refraction (n) associated with the wavelength of the radiant energy, said assembly (10) comprising: emitter means (18) for disposition on the inside of the window (12) with gas therebetween to emit radiant energy to the window (12) on an ingress axis (A) at an incident angle ($\theta$) relative to the inside surface (14), detector means (20) for disposition on the inside of the window (12) with gas therebetween to detect radiant energy from the window (12) on an engress axis (B) at a reflecton angle ($\theta'$) relative to the inside surface (14) and equal to said incident angle ($\theta$), support means (22) for spacing said emitter means (18) and said detector means (20) such that the point (I) of intersection of the ingress axis (A) with the inner surface of the window (12) from the point (E) of intersection of the engress axis (B) with the inside surface (14) of the window (12) is a predetermined distance (D), said predetermined distance (D) determined by the formula:

$$D = 2\, T \cos\theta\, (n^2 - \cos^2\theta)^{-\frac{1}{2}}$$

2. An assembly as set forth in claim 1 further characterized by said detector means (20) including limiting means (36) for limiting the field of view of radiant energy from the window (12) entering said detector means (20) by allowing to pass radiant energy substantially parallel with the egress axis (B) within the field of view.

3. An assembly as set forth in claim 2 further characterized by said detector means (20) including filter means (40) for receiving said parallel radiant energy to filter out radiant energy below a predetermined wavelength.

4. An assembly as set forth in claim 3 further characterized by said support means (22) including detector holder means (24) for supporting said detector means (20) with said egress axis (B) angled at said reflection angle ($\theta'$) directing said detector means (20) at the window (12).

5. An assembly as set forth in claim 4 further characterized by said support means (22) including emitter holder means (26) for securing said emitter means (18) with said ingress axis (A) angled at said incident angle ($\theta$) equal to said reflection angle ($\theta'$), said detector holder means (24) and said emitter holder means (26) being angled toward the window (12) at incident ($\theta$) and reflection ($\theta'$) angles greater than the critical angle of the window (12).

6. An assembly as set forth in claim 2 further characterized by said limiting means (36) including absorbing means (38) for absorbing non-parallel radiant energy to prevent the detection thereof.

7. An assembly as set forth in claim 5 further characterized by said emitter holder means (26) and said detector holder means (24) being tubular in shape and circular in cross-section, said emitter holder means (26) having an outer diameter centered about said ingress (A) axis, and said detector holder means (24) being tubular in shape and circular in cross-section having an outer diameter centered about said egress (B) axis, wherein the intersection of said emitter (26) and detector (24) holder means at said reflection ($\theta'$) and incident ($\theta$) angles with the inside surface (14) of the window (12) presents oval openings.

8. An assembly as set forth in claim 7 further characterized by said tubular emitter holder means (26) and said tubular detector holder means (24) partially overlapping at said outer diameters at the plane of the window (12), said support means (22) including blocking means (25) at said partial overlapping adjacent the window (12) for blocking radiant energy from said emitter means (18) to said detector means (20) reflected off the inside surface (14) of the window (12).

9. An assembly as set forth in claim 8 further characterized by said support means (22) encapsulating said emitter means (18) and said detector means (20), said support means (22) including openings (27) adjacent the window (12) for allowing said radiant energy to be emitted and detected.

10. An assembly as set forth in claim 2 further characterized by said support means (22) including adhering means (28) between said support means (22) and the window (12) for adhering said support means (22) to the window (12) and for preventing contamination of said emitter (18) and detector (20) means within said support means (22).

11. An assembly as set forth in claim 2 further characterized by said support means (22) including heating means (30) for removing remaining films of moisture.

12. An assembly as set forth in claim 2 further characterized by channel pairs comprising one of said emitter means (18) and said detector means (20), wherein said assembly (10) includes a plurality of said channel pairs for increased sensitivity.

13. An assembly as set forth in claim 2 further characterized by said radiant energy comprising infrared energy levels.

14. An assembly as set forth in claim 2 further characterized by said emitter means (18) including pulsing means (44) for transmitting pulses of infrared radiation toward the window (12), said pulsing means (44) including a infrared emitter diode (D1).

15. An assembly as set forth in claim 2 further characterized by said detector means (20) including detector control means (48) for receiving light energy from the window (12) and indicating when moisture or other particles have accumulated on the window (12) to actuate an indication light (D4) and a wiper.

16. An assembly as set forth in claim 2 further characterized by said support means (22) including detector holder means (24) for supporting said detector means (20) with said egress axis angled at said reflection angle to direct said detector means (20) at the window (12), and said detector holder means (24) angling said detector means (20) below the horizon.

17. A method of sensing moisture or other particles using radiant energy on a window (12) having inside (14) and outside (16) surfaces defining a thickness (T) and a of material having an index of refraction (n) associated with the wavelength of the radiant energy, said method comprising the steps of; emitting (18) radiant energy through gas to the window (12) on an ingress axis (A) at an incident angle ($\theta$) relative to the inside surface (14) of the window (12), detecting (20) the radiant energy from the window (2) through gas on an egress axis (B) at a reflection angle ($\theta'$) relative to the inside surface (14) and equal to the incident angle ($\theta$), and spacing the point (I) of intersection of the ingress axis (A) with the inner surface (14) of the window (12) from the point (E) of intersection of the egress axis (B) with the inner surface (14) of the window (12) a distance (D) which equals:

$$D = 2 T \cos \theta \ (n^2 - \cos^2 \theta)^{-\frac{1}{2}}$$

18. A method as set forth in claim 17 further including limiting (36) the field of view of radiant energy from the inside surface (14) of the window (12) for the detecting.

19. A method as set forth in claim 18 further including allowing to be detected only radiant energy substantially parallel with the egress axis (B) within the field of view.

20. A method as set forth in claim 18 further including filtering (40) light energy from the parallel radiant energy below a predetermined wavelength.

21. A method as set forth in claim 18 further including absorbing (38) non-parallel radiant energy for preventing the detection thereof.

22. A method as set forth in claim 17 further including detecting radiant energy angled above the horizon and greater than the critical angle of the window (12).

23. A method as set forth in claim 17 further including blocking emitted radiant energy reflected off the inside surface (14) of the window (12) from being detected.

24. A method as set forth in claim 17 further including pulsing (18) the radiant energy toward the inside surface (14) of the window (12) at high levels to accommodate for attenuations of radiant energy levels from the window (12), passing the radiant energy through a interlayer (42) within the window (12) attenuating the radiant energy, reflecting the radiant energy off the outside surface (16) of the window (12) attenuating the infrared energy, re-passing the radiant energy through the interlayer (42) attenuating the radiant energy for the detection thereof.

25. A sensing assembly (10) for indicating when moisture or other particles have accumulated on a window (12) having inside (14) and outside (16) surfaces and including an emitter (18) for emitting radiant energy toward the window (12), said assembly (10) comprising: detector means (20) for detecting radiant energy from the window (12) on an egress axis (B) to indicate when moisture or particles have accumulated on the window (12), said detector means (20) including collimator means (36) for limiting the field of view of radiant energy from the window (12) entering said detector means (20) by allowing to pass only radiant energy substantially parallel with the egress axis (B) within said field of view.

26. An assembly as set forth in claim 25 further characterized by said detector means (20) including filter means (40) for receiving the parallel radiant energy to filter out radiant energy below a predetermined wavelength.

27. An assembly as set forth in claim 26 further characterized by said collimator means having said filter means (40) located therewithin.

28. A sensing assembly (10) for indicating when moisture or other particles have accumulated on a window (12) having inside (14) and outside (16) surfaces and including an emitter (18) for emitting radiant energy toward the window (12), said assembly (10) comprising: detector means (20) for detecting radiant energy from the window (12) on an egress axis (B) to indicate when moisture or particles have accumulated on the window (12), said detector means (20) including limiting means (36) for limiting the field of view of radiant energy from the window (12) entering said detector means (20) by allowing to pass only radiant energy substantially parallel with the egress axis (B) within said field of view, said detector means (36) including light sensitive means (50) supported within said limiting means (36) for sensing the radiant energy.

* * * * *